United States Patent [19]

Farrington

[11] 4,280,115

[45] Jul. 21, 1981

[54] HUMIDITY SENSOR

[75] Inventor: Gregory C. Farrington, Clifton Park, N.Y.

[73] Assignee: General Electric Company, Schenectady, N.Y.

[21] Appl. No.: 49,222

[22] Filed: Jun. 18, 1979

Related U.S. Application Data

[63] Continuation-in-part of Ser. No. 878,924, Feb. 17, 1978, abandoned.

[51] Int. Cl.³ ............................................. H01L 7/00
[52] U.S. Cl. .................................. 338/35; 29/610 R; 204/195 S; 204/195 M; 422/98
[58] Field of Search ................ 338/34, 35; 73/27 R, 73/336.5; 324/65 D, 71 SN; 422/98; 23/232 E; 204/195 M, 195 S; 429/193; 29/610

[56] References Cited

U.S. PATENT DOCUMENTS

| 2,358,406 | 9/1944 | Lichtgarn | 73/335 |
|---|---|---|---|
| 2,862,090 | 11/1958 | Mayer | 338/35 |
| 3,058,079 | 10/1962 | Jones | 338/35 |
| 3,071,746 | 1/1963 | Kohl | 338/35 |
| 3,499,796 | 3/1970 | Hever et al. | 429/193 |
| 3,540,278 | 11/1970 | Diamond | 73/336.5 |
| 3,861,031 | 1/1975 | Furuichi | 29/610 |
| 3,895,271 | 7/1975 | Dudas | 73/336.5 X |
| 3,901,733 | 8/1975 | Toy et al. | 429/193 |
| 3,912,536 | 10/1975 | Galli et al. | 429/193 |
| 3,959,022 | 5/1976 | DeJonghe et al. | 136/153 |
| 4,041,437 | 8/1977 | Matsuura et al. | 338/35 |
| 4,082,826 | 4/1978 | Iijima | 264/65 |
| 4,166,009 | 8/1979 | Fray | 204/195 S |

OTHER PUBLICATIONS

Mikio Matsuura et al. Journal of the Japan Society of Powder and Powder Metallurgy, 23 (1976), 242 pp. 26–33.

Primary Examiner—C. L. Albritton
Attorney, Agent, or Firm—Jane M. Binkowski; James C. Davis, Jr.; Leo I. MaLossi

[57] ABSTRACT

A humidity sensor which responds to changes in atmospheric water content by changes in sensor impedance, has a non-porous, water impervious, ionic-conductive beta-alumina substrate, a pair of spaced apart, thin electrodes mounted on at least one major surface of the substrate, and an electrical lead in contact with each of the electrodes.

7 Claims, 3 Drawing Figures

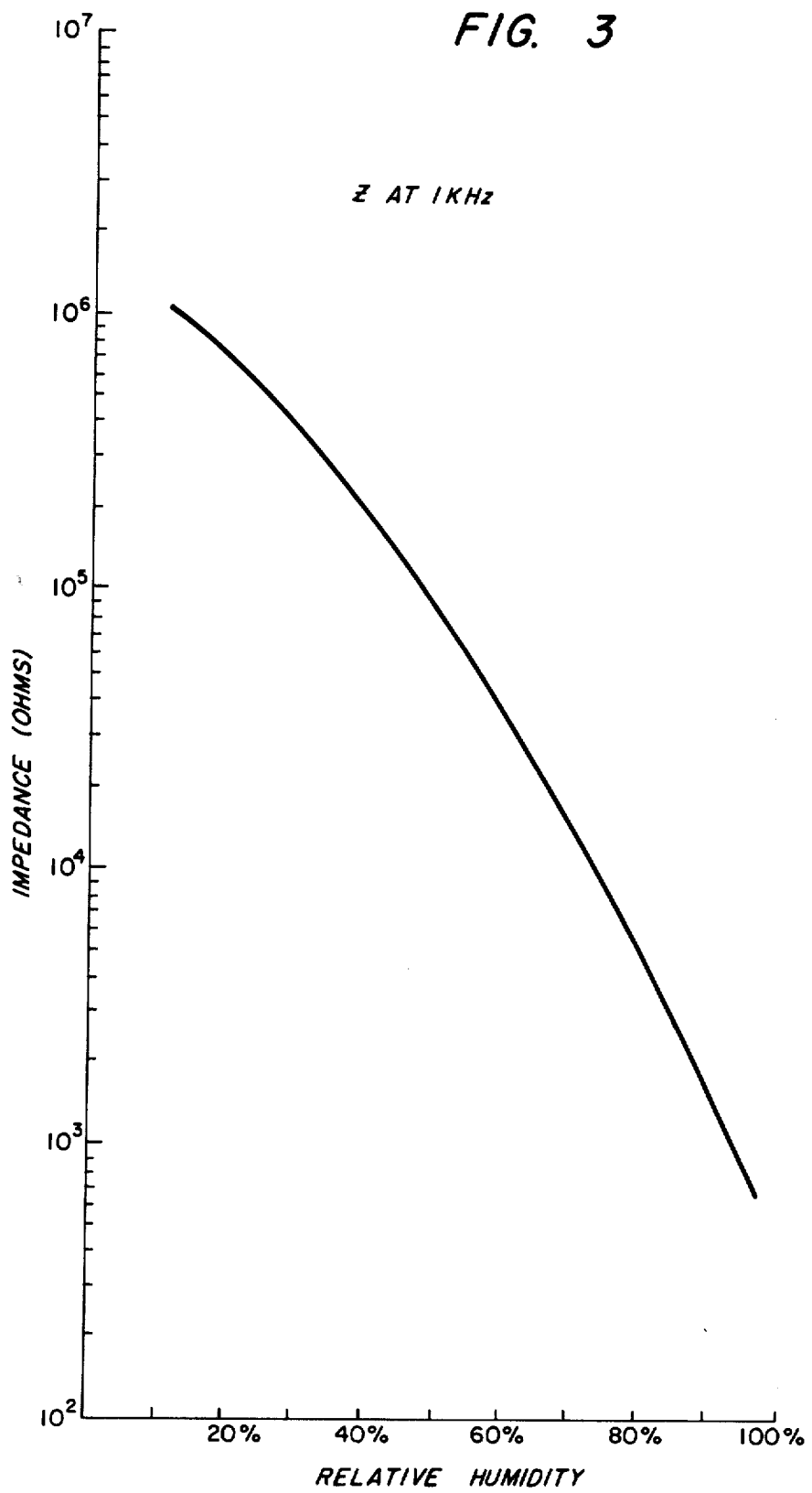

HUMIDITY SENSOR

This application is a continuation-in-part application of copending patent application Ser. No. 878,924, filed Feb. 17, 1978, now abandoned, under the same title. This application is assigned to the same assignee as application Ser. No. 878,924.

This invention relates to a humidity sensor and, more particularly, to such a humidity sensor with a water impervious, ionic-conductive beta-alumina substrate which sensor responds to changes in atmospheric water content by changes in sensor impedance.

A substantial increase in the need for accurate humidity measurement and control devices has occurred during the last decade. Areas of science and technology which has traditionally used humidity sensors, and include meteorology, the processing and storage of foods, textiles and chemicals. Such areas require increasing numbers of such devices with a greater degree of precision and accuracy in their operation. New awareness of the importance of humidity control for human health and comfort has resulted in the increased use of humidifier and dehumidifier devices. The aerospace and computer technologies have likewise created new demands for humidity sensors.

A wide range of humidity sensors have been developed in recent years in response to these needs. In spite of these developments, however, the need for an accurate, reliable, yet inexpensive sensor for general purpose humidity measurement and control has not been adequately met.

The most widely used types of sensors for humidity measurement and control applications are the mechanical, wet-bulb, and electrical types. Of these, the mechanical sensors, which depend upon the dimensional changes produced in certain materials by changes in humidity, are by far the most popular. The materials employed here are generally either hair or nylon fiber. Their elongation and contraction can be used to move a pointer on a dial, activate a microswitch, or open a valve for humidity measurement or control purposes. The relative simplicity and low cost of the mechanical devices have contributed greatly to their popularity. However, they leave much to be desired in terms of accuracy, sensitivity, and reliability. Severe hysteresis, slow response, and a drift in calibration due to stretching of the fibers are characteristic of these devices.

Wet-bulb type sensors depend upon the lowering in temperature which occurs upon evaporation of moisture from a surface; the magnitude of the lowering in temperature is a function of the relative humidity. These devices generally use simple mercury thermometers as the temperature sensors and are widely used for humidity measurement. Modifications using thermistors as the temperature sensors have also been used for control purposes. However, the relatively high cost and frequent maintenance required for wet-bulb sensor control devices limit their usefulness in this respect.

Electrical sensors have also found widespread use for the measurement of relative humidity, particularly in scientific applications such as meteorology, where they are employed for remote measurements of the atmospheric moisture content. These sensors commonly consist of an ionic salt, such as LiCl, in an organic binder or a porous substrate; appropriately spaced electrodes are used to make electrical contact. Their response characteristics are quite dependent upon the nature of the salt, the substrate and the electrode system used. In general, they are more sensitive, more accurate, are less subject to drift, and have a more rapid response than the mechanical sensors. On the other hand, they are generally more expensive, and are easily contaminated and damaged by foreign substances in the air and by condensation of water on their surface. The high impedance of most of these devices, particularly at low RH, their limited range, and their high cost have restricted their usage for control applications.

An electronic sensor is described in an article entitled "Humidity Dependence Resistivity of Potassium-Modified Ferric Oxide Ceramics" by M. Matsuura et al. in the *Journal of the Japan Society of Power and Powder Metallurgy,* 23, 1976, pages 242–249. The article describes potassium-modified ferric oxide ceramics which are water pervious and porous thereby showing bulk-type sensitivity for ambient humidity. On page 234, it is pointed out that fired-on silver electrodes were applied to the both surfaces of the sintered discs.

The sensor described in the above article from the *Journal of the Japan Society of Power and Powder Metallurgy* has a potassium-modified ferric oxide ceramic which shows bulk-type sensitivity for ambient humidity. This sensor, which is water pervious and porous thereby, has a bulk effect and is subjected to the disadvantage of water diffusion into the ceramic resulting in less reliable sensitivity and frequent re-calibration. As opposed to the sensor in the above article, the sensor of the present invention has a non-porous, water impervious ionic-conductive substrate which is most stable in the presence of liquid water resulting in more reliable sensitivity and infrequent calibration. The present sensor has a surface effect because it is non-porous and water impervious as opposed to the bulk effect of the sensor described in the above article, which latter sensor is both water pervious and porous.

In U.S. Pat. No. 2,862,090-Mayer, there is described an apparatus for determining moisture, wherein the humidity-sensitive member comprises a core of cerium titanate and a pair of spaced electrodes in intimate contact therewith. This patent has essentially a non-conductive ceramic which has water surface conductivity as opposed to the present sensor which has an ionic-conductive ceramic of solid beta-alumina. The humidity sensor of the present application provides a more conductive device.

U.S. Pat. No. 2,358,406-Lichtgarn relates to a humidity responsive device which includes a humidity responsive resistance element. Element 12 is described on page 2, column 2, lines 71–75 as being formed from a material which has a relatively low conductivity, is highly porous and is capable of absorbing water from the atmosphere. This resistance element is further described on page 4, column 1, lines 66–75, page 4, column 2, lines 1–75, page 5, column 1, lines 1–75 and page 5, column 2, lines 1–58. Further, page 4, column 2, lines 61–75 lists a number of highly porous materials which can be employed, including alumina.

U.S. Pat. No. 3,540,278-Diamond relates to a moisture sensor wherein the substrate material is preferably somewhat porous and hygroscopic so that the moisture will be quickly absorbed and slowly given off. Further, the substrate is pointed out as being electrically insulating and may be a ceramic material.

U.S. Pat. No. 3,895,271-Dudas relates to a moisture sensor which includes flattening part of an aluminum wire, oxidizing at least the flat surface of the flattened wire, and providing a layer of the second metal over at least a part of the oxidized surface. The oxide layer is hygroscopic so that it will absorb moisture from the surrounding atmosphere. Further, the metal applied over at least a portion of the oxide layer is provided with fine cracks to facilitate penetration of water vapor to the underlying oxide.

U.S. Pat. No. 4,082,826-Iijima relates to a process for producing highly ion-conductive porcelain. The process involves producing a beta-alumina/beta"-alumina powder to which is added a small weight percent of a compound capable of providing a monovalent or divalent metal ion. The mixture is molded and sintered in an alkaline atmosphere.

As opposed to the above Lichtgarn and Diamond patents, applicant's humidity sensor has a non-porous, water impervious ionic-conductive beta-alumina substrate. Both of the above patents describe humidity sensitive devices in which the humidity responsive resistance element or substrate is porous and capable of absorbing water from the atmosphere.

The subject Dudas patent has a hygroscopic oxide layer, which is not ionic-conductive and which will absorb moisture from the surrounding atmosphere as opposed to applicant's nonporous, water impervious substrate. The above Iijima patent relates to a process for producing highly ion-conductive porcelain.

Of the wide variety of other devices currently available for general purpose humidity measurement and control applications, none exhibit the unique objects of simplicity, ruggedness and accuracy toward a wide variety of environmental conditions and low cost, which are characteristic of the sensor to which our present invention is directed.

In accordance with one aspect of our invention, a humidity sensor has a non-porous, water impervious ionic conductive beta-alumina substrate, a pair of spaced apart, thin electrodes mounted on at least one major surface of the substrate and an electrical lead in contact with each of the electrodes.

These and various other objects, features and advantages of the invention will be better understood from the following description taken in connection with the accompanying drawing in which:

FIG. 3 is a graph showing equilibrium response of a humidity sensor of my invention in which sensor impedance in ohms ($\Omega$) is plotted against percentage of relative humidity (RH).

Figure 1:
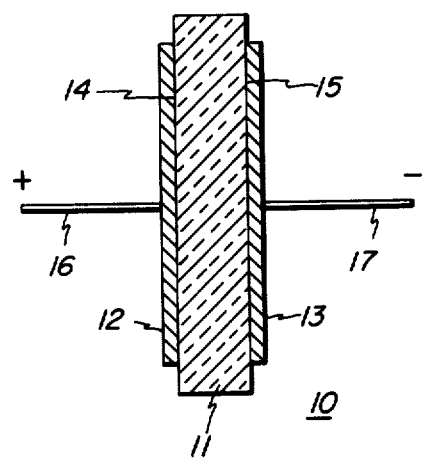
FIG. 1 is a sectional view of a humidity sensor made in accordance with my invention.

In FIG. 1 of the drawing, there is shown generally at 10 a humidity sensor made in accordance with our invention. Sensor 10 is shown with a non-porous, water impervious, ionic conductive beta-alumina substrate 11 of sodium beta-alumina. A pair of spaced apart, thin silver electrodes 12 and 13 are mounted on opposite major surfaces 14 and 15 of substrate 11. Electrical leads 16 and 17 are in contact with electrodes 12 and 13, respectively.

Figure 2:
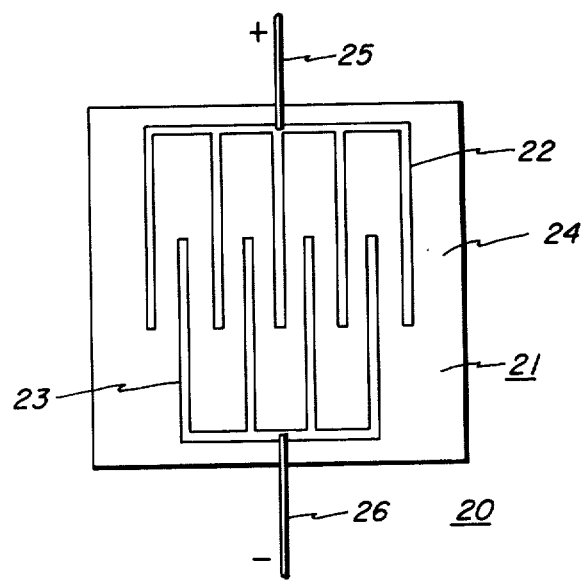
FIG. 2 is a side elevational view of a modified humidity sensor made in accordance with my invention.

In FIG. 2 of the drawing, there is shown generally at 20 a modified humidity sensor made in accordance with our invention. Sensor 20 is shown with a non-porous, water impervious, ionic-conductive beta-alumina substrate 21 of sodium beta-alumina. A pair of spaced apart, thin inter-digitated silver electrodes 22 and 23 are mounted on one major surface 24 of substrate 11. Electrical leads 25 and 26 are in contact with electrodes 22 and 23, respectively.

In FIG. 3, there is shown a graph showing equilibrium response of a humidity sensor in which sensor impedance in ohms ($\Omega$) is plotted against percentage of relative humidity (RH). The sensor had a non-porous, water impervious, ionic conductive sodium beta-alumina substrate with a thin silver electrode mounted on each of the opposite major surfaces of the substrate. An electrical lead was in contact with each of the electrodes.

I found that I could form an improved humidity sensor which responds to changes in atmospheric water content by a change in sensor impedance. The improved humidity sensor has a non-porous, water impervious ionic-conductive beta-alumina substrate, a pair of spaced apart, thin electrodes mounted on at least one major surface of the substrate, and an electrical lead in contact with each of the electrodes.

The term non-porous, water impervious, ionic-conductive beta-alumina as used in the present application includes beta-alumina, beta"-alumina, mixtures thereof and related compounds which have alkali, silver or hydrogen ions. Suitable alkali ions include sodium, potassium, lithium and mixtures thereof, such as lithium-sodium.

The electrodes are thin and are made of metals which can be applied to the substrate in a variety of manners. The spaced apart electrodes can be in various configurations such as strips, rings, interdigitations, etc. The spaced apart electrodes are mounted on one or both major surfaces of the substrate. The phrase "a pair of spaced apart, thin electrodes mounted on at least one surface of the substrate" as used in this application is intended to include mounting on one or both major surfaces of the substrate. If the electrodes are mounted on both major surfaces of the substrate, one electrode is mounted on each such major surface of the substrate. The electrodes can be deposited on the substrate, for example, by evaporation or sputtering.

The non-porous, water impervious, ionic-conductive alkali beta-alumina substrate provides ionic-conductivity between the thin electrodes mounted thereon. The non-porous, water impervious, ionic-conductive beta-alumina can be produced in various manners known in the art. I prefer to use isostatic pressing, which is known in the art, to form the non-porous, water impervious, ionic-conductive beta-alumina substrate.

My present sensor includes, for example, a non-porous, water impervious ionic-conductive sodium beta-alumina substrate with a silver electrode evaporated on at least a portion of each major surface of the substrate. An electrical lead is connected to each electrode. When this sensor is tested for relative humidity vs. impedance characteristics, the variation of electrical resistance with relative humidity was determined using a continuous flow controlled humidity air stream and and AC conductance bridge. The humidity air streams were equilibrated at room temperature and then mixed in various controlled proportions to regulate the flows to determine the relative amounts being mixed. The subject sensor is useful over various temperature ranges such as 0° C. to 100° C.

Examples of humidity sensors made in accordance with my invention are as follows:

EXAMPLE 1

A humidity sensor was made as described above and as shown in FIG. 1 of the drawing. This sensor was formed from a non-porous, water impervious ionic-conductive sodium beta-alumina substrate, which substrate had been produced in the form of a disc employing initially isostatic pressing and subsequent sintering. A silver electrode was evaporated on a portion of each major surface of the substrate. An electrical lead was connected to each electrode. This device is a humidity sensor made in accordance with my invention.

EXAMPLE 2

A humidity sensor was made as described above and as shown in FIG. 1 of the drawing. This sensor was formed from a non-porous, water impervious, ionic-conductive sodium beta-alumina substrate, which substrate has been produced in the form of a disc employing initially isostatic pressing and subsequent sintering. A gold electrode was evaporated on a portion of each major surface of the substrate. An electrical lead was connected to each electrode. This device is a humidity sensor made in accordance with my invention.

EXAMPLE 3

A humidity sensor was made as described above and as shown in FIG. 1 of the drawing. This sensor was formed from a non-porous, water impervious ionic-conductive potassium beta-alumina substrate, which substrate had been produced in the form of a disc employing initially isostatic pressing and subsequent sintering. A silver electrode was evaporated on a portion of each major surface of the substrate. An electrical lead was connected to each electrode. This device is a humidity sensor made in accordance with my invention.

EXAMPLE 4

A humidity sensor was made as described above and as shown in FIG. 1 of the drawing. This sensor was formed from a non-porous, water impervious ionic-conductive silver beta-alumina substrate, which substrate had been produced in the form of a disc employing initially isostatic pressing and subsequent sintering. A platinum electrode was evaporated on a portion of each major surface of the substrate. An electrical lead was connected to each electrode. This device is a humidity sensor made in accordance with my invention.

EXAMPLE 5

The sensor of Example 1 was tested for relative humidity vs. impedance characteristics wherein the variation of electrical resistance with relative humidity was determined, using a continuous flow controlled humidity air stream and an AC conductance bridge. The humidity air stream was equilibrated at room temperature and then mixed in continuously controlled proportions to regulate the flows to determine the relative amounts being mixed. The results of this testing are shown in the graph in FIG. 3 of the drawing, which testing was accomplished at 25° C.

While other modifications of the invention and variations thereof, which may be embraced within the scope of the invention have not been described, the invention is intended to include such as may be embraced with the following claims:

What I claim as new and desire to secure by Letters Patent of the United States is:

1. A humidity sensor responsive to changes in atmospheric water content by changes in sensor impedance which consists essentially of a nonporous, water impervious ionic-conductive beta-alumina substrate, at least a pair of spaced apart, thin electrodes mounted on at least one major surface of the substrate, and an electrical lead in contact with each of the electrodes.

2. A humidity sensor as in claim 1, in which a thin electrode is mounted on each opposite major surface of the substrate.

3. A humidity sensor as in claim 1, in which the electrodes are spaced apart and interdigitated on one major surface of the substrate.

4. A humidity sensor as in claim 1, in which the beta-alumina is sodium beta-alumina.

5. A humidity sensor as in claim 1, in which the beta-alumina is sodium beta-alumina, and the electrodes are silver.

6. A humidity sensor as in claim 1, in which the beta-alumina is sodium beta-alumina, and the electrodes are gold.

7. A humidity sensor as in claim 1, in which the beta-alumina is potassium beta-alumina.

* * * * *